(12) United States Patent
Fukushima et al.

(10) Patent No.: US 10,568,544 B2
(45) Date of Patent: Feb. 25, 2020

(54) 2-DIMENSIONAL THERMAL CONDUCTIVE MATERIALS AND THEIR USE

(71) Applicants: Hiroyuki Fukushima, Lansing, MI (US); Thomas Ritch, East Lansing, MI (US); Jessica Russell, Webberville, MI (US); Liya Wang, Ann Arbor, MI (US)

(72) Inventors: Hiroyuki Fukushima, Lansing, MI (US); Thomas Ritch, East Lansing, MI (US); Jessica Russell, Webberville, MI (US); Liya Wang, Ann Arbor, MI (US)

(73) Assignee: XG Sciences, Inc., Lansing, MI (US)

( * ) Notice: Subject to any disclaimer, the term of this patent is extended or adjusted under 35 U.S.C. 154(b) by 308 days.

(21) Appl. No.: 15/285,967

(22) Filed: Oct. 5, 2016

(65) Prior Publication Data

US 2017/0101571 A1    Apr. 13, 2017

Related U.S. Application Data

(60) Provisional application No. 62/284,797, filed on Oct. 9, 2015.

(51) Int. Cl.
*C09K 5/10* (2006.01)
*H05K 7/20* (2006.01)
(Continued)

(52) U.S. Cl.
CPC ............ *A61B 5/103* (2013.01); *A61B 3/0025* (2013.01); *A61B 3/112* (2013.01); *A61B 5/0059* (2013.01); *A61B 5/1104* (2013.01); *A61B 5/1107* (2013.01); *A61B 5/4824* (2013.01); *A61B 3/145* (2013.01); *B32B 15/08* (2013.01); *B82Y 30/00* (2013.01); *F28F 3/00* (2013.01); *F28F 13/18* (2013.01); *F28F 19/02* (2013.01); *F28F 2013/005* (2013.01); *F28F 2245/06* (2013.01); *H05K 7/20509* (2013.01)

(58) Field of Classification Search
CPC ...... H05K 7/20509; F28F 19/02; F28F 13/18; F28F 3/00; F28F 2013/005; F28F 2013/006; F28F 2245/06; B32B 15/08; B82Y 30/00
USPC ........................................................ 165/185
See application file for complete search history.

(56) References Cited

U.S. PATENT DOCUMENTS 7,886,813 B2    2/2011  Hua et al.
2001/0048172 A1   12/2001  Smith et al.
(Continued)

FOREIGN PATENT DOCUMENTS

WO    WO2015/103435    9/2015

OTHER PUBLICATIONS

International Search Report dated Dec. 27, 2017 for International Application No. PCT/US2016/055873 filed Oct. 7, 2016.

*Primary Examiner* — Joel M Attey
(74) *Attorney, Agent, or Firm* — Avery N. Goldstein; Blue Filament Law PLLC

(57) ABSTRACT

The development and manufacture of thermal interface materials including, among other forms, greases, pastes, gels, adhesives, pads, sheets, solders and phase change materials, with good through-plane thermal conductivity for thermal interface applications. The good through-plane thermal conductivity is achieved through the formation of a conductive network by the use of thermal conductive material-coated fillers, combinations of thermal conductive material-coated fillers and uncoated fillers.

18 Claims, 4 Drawing Sheets

(51) Int. Cl.
*A61B 5/103* (2006.01)
*A61B 5/00* (2006.01)
*A61B 3/11* (2006.01)
*A61B 5/11* (2006.01)
*A61B 3/00* (2006.01)
*A61B 3/14* (2006.01)
*F28F 19/02* (2006.01)
*B82Y 30/00* (2011.01)
*F28F 3/00* (2006.01)
*B32B 15/08* (2006.01)
*F28F 13/18* (2006.01)
*F28F 13/00* (2006.01)

(56) References Cited

U.S. PATENT DOCUMENTS

| | | |
|---|---|---|
| 2008/0118736 A1 | 5/2008 | Drzal et al. |
| 2008/0291634 A1 | 11/2008 | Weiser et al. |
| 2009/0008779 A1 | 1/2009 | Suhir et al. |
| 2011/0308782 A1 | 12/2011 | Merrill et al. |
| 2012/0080639 A1 | 4/2012 | Bruzda et al. |
| 2013/0221268 A1 | 8/2013 | Sung et al. |
| 2014/0011034 A1* | 1/2014 | Majumder .............. C02F 1/288 428/406 |
| 2014/0025578 A1 | 1/2014 | Evans |
| 2014/0085813 A1 | 3/2014 | Sedarous |
| 2014/0120399 A1 | 5/2014 | Balandin |
| 2014/0255785 A1* | 9/2014 | Do .......................... C09D 1/00 429/231.8 |
| 2014/0328024 A1 | 11/2014 | Mataya et al. |
| 2014/0345843 A1* | 11/2014 | Kirkor ................... F28F 23/00 165/185 |
| 2015/0014577 A1 | 1/2015 | Chowdhury et al. |
| 2015/0148459 A1 | 5/2015 | Pawloski et al. |
| 2016/0169598 A1* | 6/2016 | Semenic ............... F28F 13/003 165/185 |

* cited by examiner

2-DIMENSIONAL THERMAL CONDUCTIVE MATERIALS AND THEIR USE

This application is a utility application form, and claims priority from U.S. Provisional patent application Ser. No. 62/284,797 filed Oct. 9, 2015.

SUMMARY OF THE INVENTION

This invention deals with the development and manufacture of graphene based thermal interface materials including, among other, greases, pastes, gels, adhesives, pads, sheets, solders and phase change materials, with good through-plane thermal conductivity for thermal interface applications. The good through-plane thermal conductivity is achieved through the formation of a conductive network by the use of the graphene and graphene-coated fillers.

BACKGROUND OF INVENTION

Thermal interface materials (TIM) are used to minimize the contact thermal resistance between a heat source and a heat sink. It is widely applied in electronic and other industries where heat removal from chips or processors is critical since operation of integrated circuits at elevated temperatures is a major cause of failure for electronic devices. Such thermal management is becoming more and more important with the rapidly increasing functions and hence power densities of advanced electronics. Generated heat needs to be transferred or dissipated to a heat, sink in order to maintain an appropriate operating temperature.

When two solid surfaces, such as a heat source and a heat sink, are put together, however, the real contact area between them is limited due to the fact that the two surfaces are not completely flat, only a very small portion of the apparent surface area is actually in contact. As a result, thermal transfer between these mating surfaces is very limited as well, causing a notable temperature difference at the interface. The major role of TIMs is to fill the gap between the two mating surfaces and increase the heat transfer between them. The major requirements for a TIM material are: high thermal conductivity, easily deformed by a small pressure to fill the void between the contacting surfaces, good wetting and affinity with the two contacting surfaces, ability to form a layer with minimal thickness, mechanically stable, not easy to leak out, good thermal cycle life, and, easy to apply.

Traditional TIMs include greases, pads, gels, adhesives, solders, and phase change materials, etc. Most of them are made of a polymer or silicone matrix loaded with thermally conductive filler particles.

Thermal greases are a form of thick paste composed of thermally conductive filler dispersed in silicone or hydrocarbon oil. The filler can toe metallic, ceramic, or carbonaceous materials. Metal-based thermal greases often employ silver, copper, or aluminum particles. They usually have good thermal conductivity, but may suffer high cost.

Additionally, they are electrically conductive which may limit their applications without an additional electrically insulating material to go with them. Ceramic-based thermal pastes typically use conductive ceramic particles, such as beryllium oxide, aluminum nitride, aluminum oxide, zinc oxide, and silica as the filler. They usually have good thermal conductivity and low cost. Carbon-based thermal greases are relatively new. Good fillers include carbon nanotube (CNT) and carbon nano fibers (CNF). In general, thermal greases have high thermal conductivity, thin bond line thickness (BLT) with minimal pressure, low viscosity to fill the voids between mating surfaces, and no need to be cured. However, thermal grease is susceptible to grease pump-out and messy to apply. The pump-out is typically caused by mismatched coefficients of thermal expansion (CTE) of the mating surfaces, which could force the TIM to flow out of the interface by alternately squeezing and releasing the system during thermal cycling.

Thermal pads are a group of TIMs in the form of pad. They typically consist of an elastomer matrix such as silicone rubber and thermally conductive fillers such as boron nitride, alumina, or sine oxide. The material is often made into a soft pad that can be conformable to the mating surfaces upon compression, they are easily handled and applied, less susceptible to pump-out, and can serve as a vibration damper. Their major drawbacks include the need for high contact pressure and lower thermal conductivity and higher costs than thermal greases.

Thermal gels typically consist of silicone (or olefin) polymers with low cross-lint density loaded with a thermally conductive filler, either ceramic or metallic. The silicone has low modulus of elasticity, good wetting characteristics and high thermal stability. The materials are like greases but can be cured. They have relatively decent thermal conductivity, good wetting characteristics, easy to conform to mating surfaces, and are less susceptible to pump out. However, they need to be cured and may delaminate during thermal cycling.

Thermal adhesive; are a type of thermally conductive glue normally consisting of an adhesive resin and a thermally conductive filler. An example is silver particles dispersed in a cured epoxy matrix. Such TIMs eliminate the need for mechanical attachment of permanent pressure and are easy to apply. They are not susceptible to pump-out and can conform to the mating surfaces. However, they need to be cured and there is a risk of delamination during usage.

A phase change material (PCM) is a substance with a high heat of fusion which is capable of storing or releasing a large amount of energy upon melting or solidifying. The phase change thermal, interface materials are typically made of suspended particles of high thermal conductivity and a base material. Examples include conductive metal oxide particles dispersed in an organic matrix such as fully refined paraffin, a polymer, a co-polymer, or a mixture of the three. At room temperatures, they are similar to thermal pads. When heated, to a certain temperature, normally >50° C., they change to semi-solids or liquids to fill the void between mating surfaces. They solidify again when the temperature drops below the transition temperature. PCM is less susceptible to pump-out and its application is easier than grease. It also does not need to cure and there is no delamination concern. The major drawbacks are their lower conductivity as compared to that of grease and a pressure is required as well.

The thermal conductivity of commercially available TIMs is around 5 W/mK which is considerably lower than those of the typical mating surfaces. As a result, there has been a growing interest in searching for better TIMs, especially more effective fillers. Advanced carbon-based nano materials such as carbon nanotube, graphene, and graphene nano-platelets are promising candidates due to their high intrinsic thermal conductivities. For example, the thermal conductivity of single-wall carbon nanotube (CNT) is in the range of 3000-5000 W/mK at room temperature whereas that of graphene is even higher. While CNT has received considerable attention for TIM applications, it has yet to foe commercially successful due to both performance and manufacturing cost issues. Early work focused on dispersing CNT randomly and the results have been less satisfactory.

Recently, attention has shifted to the vertical alignment of CNT and reduction of boundary resistance at the interface between CNT and two mating surfaces. But, it will be a challenge for such a technology to be used for mass application due to its high processing costs.

Recently, graphene became a new focus for advanced thermal management solutions due to its high thermal conductivity. Graphene has a unique thermal property: it has an extremely high in-plane thermal conductivity but the through-plane conductivity of graphene is at least two orders of magnitude lower. The high in-plane thermal conductivity results from the covalent $sp^2$ bonding between carbon atoms whereas the poor through-plane thermal conductivity is mainly due to weak van der Waals coupling in that direction. The thermal conductivity of a suspended monolayer graphene was reported to be about 5000 W/mK when measured by an optical method from shift in Raman G band. It's for this reason attempts have been made by many investigators to incorporate graphene or graphene nanoplatelets in various materials or forms for thermal applications including sheet products for thermal dissipation and graphene-based pastes/adhesives for thermal interface heat transfer.

For example, the inventors herein have developed a graphene-based sheet product (XG Leaf B) that can be used for spreading heats from a heat source to a heat sink. The material has a high in-plane thermal conductivity of >500 W/mK and a low through-plane conductivity of <5 W/mK. This material utilizes the 2-dimensional and anisotropic features of graphene nanoplatelets so that heat is dissipated laterally away from heat source instead of transferring through to other parts of electronic devices. For some other applications, however, heat needs to be transferred across two mating surfaces of a heat source and a heat sink. For example, FIG. 1 shows an application of thermal interface material in a LED lighting device. Currently, silver-based solder paste is used to transfer heat away from LED chip to a heat sink. There are several disadvantages with this thermal management solution. First, the paste needs to be cured at a temperature that can easily cause damage to the chips. Second, once cured, it is very difficult to be taken apart. When one chip fails, the entire unit has to be replaced. Third, silver-based paste is expensive. As a result, it is desired to replace the solder paste with a thin grease, gel, or tape with a high through-plane thermal conductivity and low cost. Some other applications require the TIM to be in the form of an adhesive, pad, phase change materials, and the like. It was under this circumstance that following inventions were conceived.

Graphene and graphene-based materials have been used in thermal interface materials as a filler as found in WO2015/103435, US2014/328024, and US2014/120399. Due to their 2-dimensional, nature, however, graphene sheets or graphene nanoplatelets tend to align or orient parallel, to the thermal interface, especially under pressure. As a result, the effect in enhancing the thru-plane thermal conductivity is substantially diminished. Therefore, it is imperative to establish a thermal pathway that can effectively conduct heat in the through plane direction. The instant invention has unique distinctions over the prior art.

WO2015/103435, deals with a method of aligning graphene flakes perpendicular to the mating substrate using magnetic functionalization and magnetic fields. This requires expensive specialized equipment to generate the magnetic fields. Additionally, the graphene alignment may decrease over time, in a fluid system, once the magnetic field is no longer applied. In the instant invention, graphene, graphene nanoplatelets, or toher thermally conductive materials such as boron nitride platelet can be coated or anchored on the surface of fillers. The partial graphene platelet alignment perpendicular to the mating substrates is an inherent property of a TIM made with graphene or another coated filler, and will remain stable. Such a TIM can be processed using standard industry equipment and methods and still get the benefit of aligned, graphene and other thermally conductive platelets.

US2014/120399 describes the thermal benefits of adding graphene to a matrix for use as a TIM, but makes no mention of the problem of platelet alignment encountered in the thin bond lines used in practical TIM applications. Our instant invention addresses that alignment problem.

US2013/0221268 describes a thermal paste using graphene platelets in conjunction with other filler materials to create a 3D conductive network. However, by coating the graphene platelets onto the other fillers without significantly damaging their structure the instant invention achieves similar thermal conductivity improvement with greatly reduced viscosity, resulting in a superior product for handling and thermal resistance.

U.S. Pat. No. 7,886,813 describes a TIM material with filler particles coated with high thermal conductivity coatings. The coatings are metals and the use of a graphite or a sheet material to coat the fillers is not contemplated.

U.S. 2014/025578 describes 3 process for coating particles with graphene. Use of such particles for heat transfer such as in a TIM is not contemplated.

THE INVENTION

Thus, in one embodiment of this invention, there is a thermal interface material containing a material selected from the group consisting of fillers, graphene coated fillers, and, mixtures of fillers and graphene coated fillers.

In another embodiment, there is a method, of providing a thermal interface composite, the method comprising providing a first substrate that is a heat sink and providing a second substrate that is a heat source, and placing a thermal interface material as described herein between the first substrate and the second substrate.

There is a further embodiment, which is a composite structure comprising a solid heat source, a solid heat sink, and, a thermal interface material as described, herein contained between the solid neat source and the solid heat sink.

Figure 1:
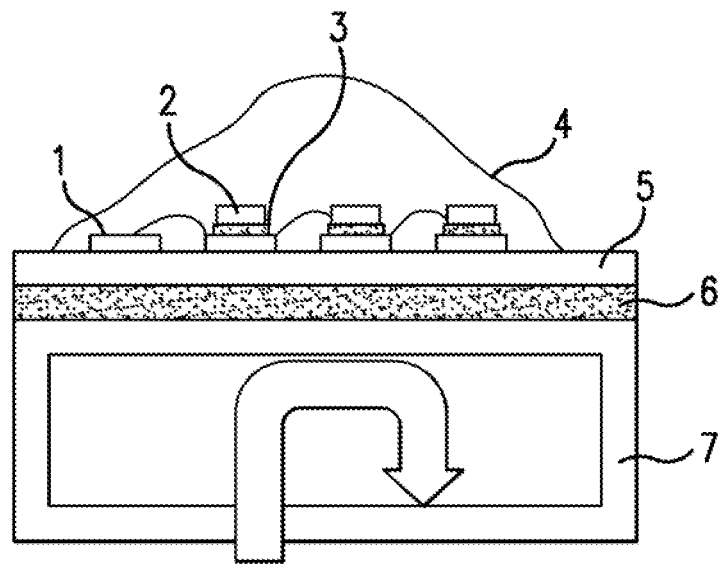
FIG. 1 is an exemplary application illustration of thermal interface material showing a pad on an AlN board 1, LED chip 2, thermal interface material 3, silicon 4, AlN board 5, thermal interface material 6, and heat sink 7.
Figure 2:
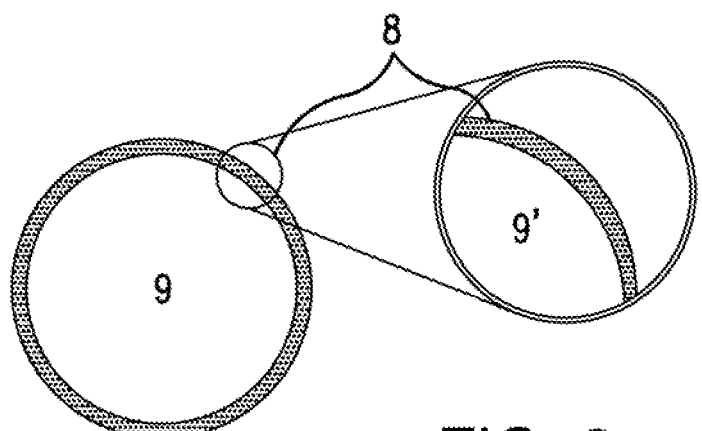
FIG. 2 is an illustration of a nanoplatelet coated filler particle showing the graphene coating 8 and the filler particles 9 and 9'.

In the instant invention, a through-plane thermal pathway can foe achieved through two approaches:

1. Use of nanoplatelet-coated filler particles. For example, ceramic particles can be coated by a highly conductive nanoplatelet material such as graphene nanoplatelet and boron nitride platelet. The coating helps ensure a vertical heat, conducting pathway with a; minimum amount of graphene nanoplatelet addition. FIG. 2 illustrates this concept.

Figure 3:
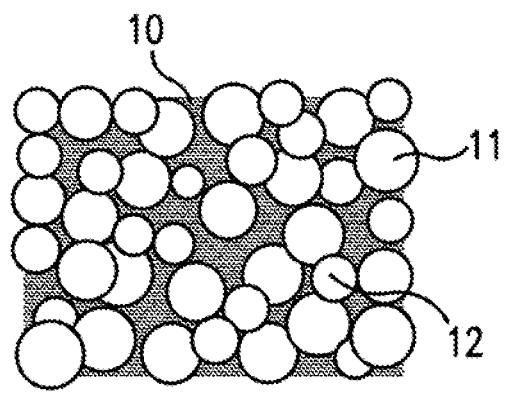
FIG. 3 is an illustration of a thermal interface material made with thermally conductive nanoplatelets and nanoplatelet coated fillers showing the resin matrix 10, the graphene coated filler particle 11, the graphene sheet or graphene nanoplatelet 12.

2. Use of fillers with different sizes and morphologies. For example, in one embodiment, nano-platelet coated spherical filler particles are used together with graphene nanoplatelets to form a 3-D conductive network better than using spherical particles alone. The additional graphene nanoplatelets serve to better bridge the fillers with improved contact due to the 2-D and flexible feature of graphene nanoplatelets as illustrated in FIG. 3. For example, the contact between two spheres is theoretically a single point contact. Introduction of flexible and flake-like graphene nanoplatelets can significantly increase the contact area of conductive fillers.

Figure 4:
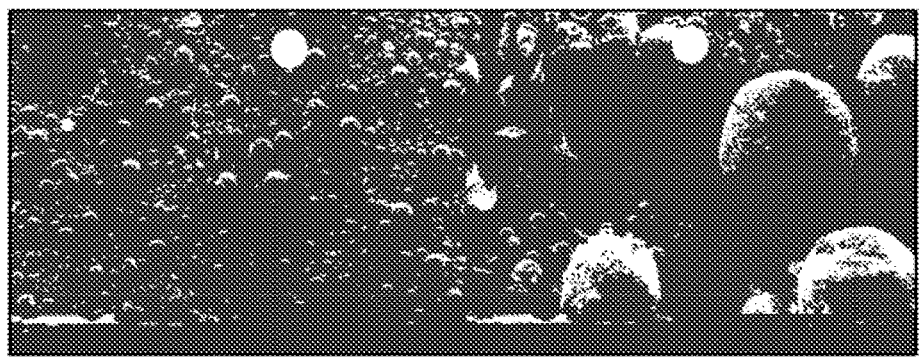
FIG. 4 is a microphotograph of graphene nanoplatelet coated alumina fillers for thermal interface materials.
Figure 5:
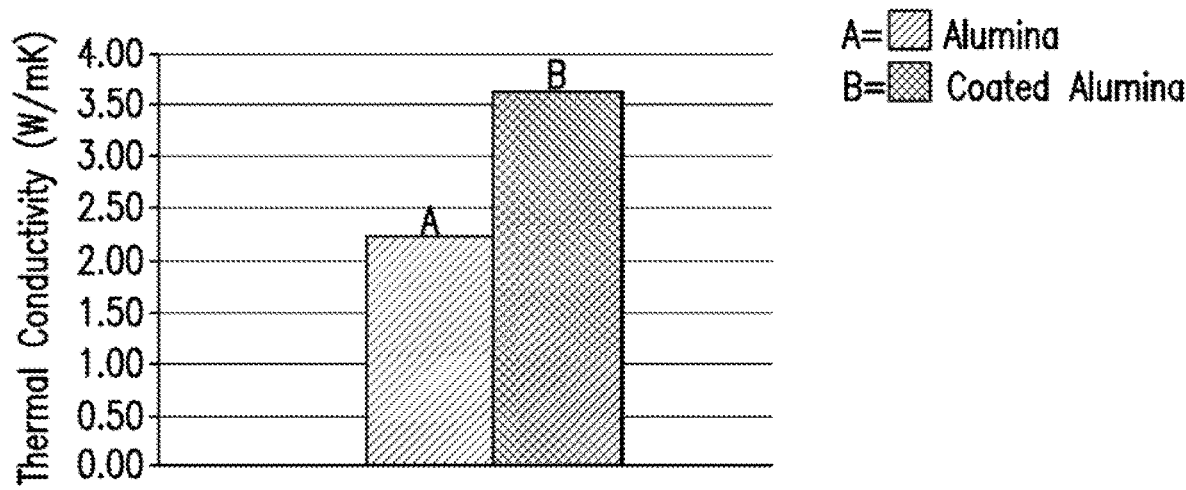
FIG. 5 is a graph of thermal conductivity of alumina of the prior art compared to coated alumina of the instant invention.
Figure 6:
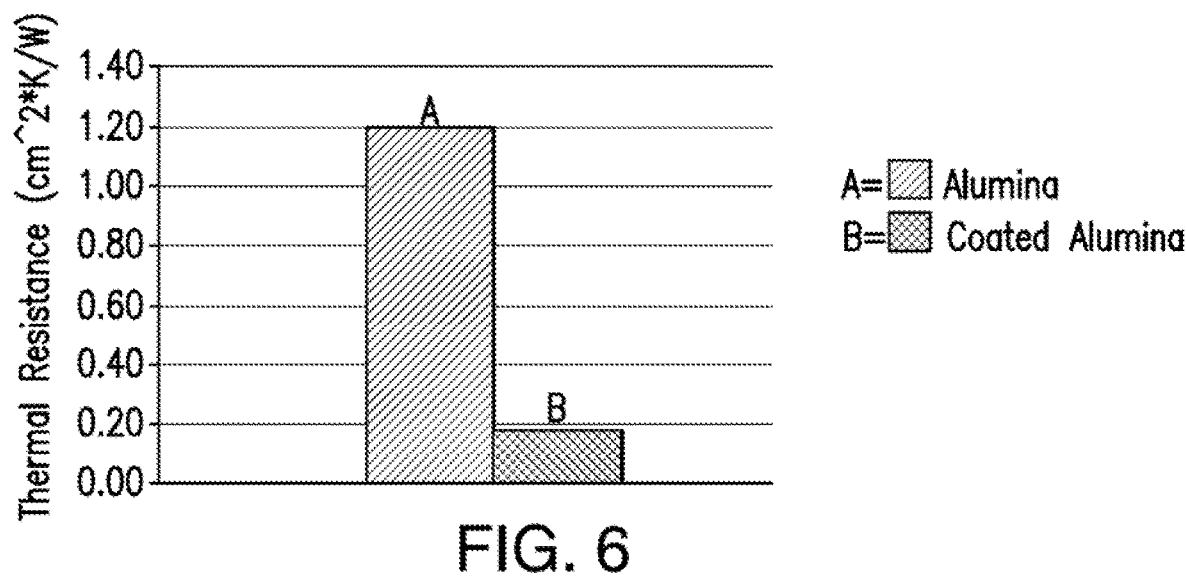
FIG. 6 is a graph of thermal resistance of alumina of the prior art compared to coated alumina of the instant invention.
Figure 7:
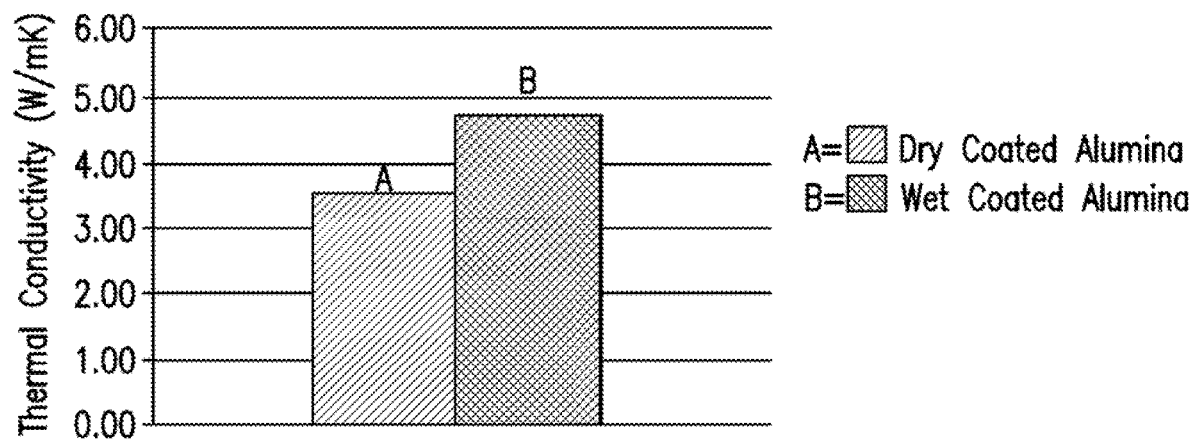
FIG. 7 is a graph of thermal conductivity showing dry coated alumina versus wet coated alumina.
Figure 8:
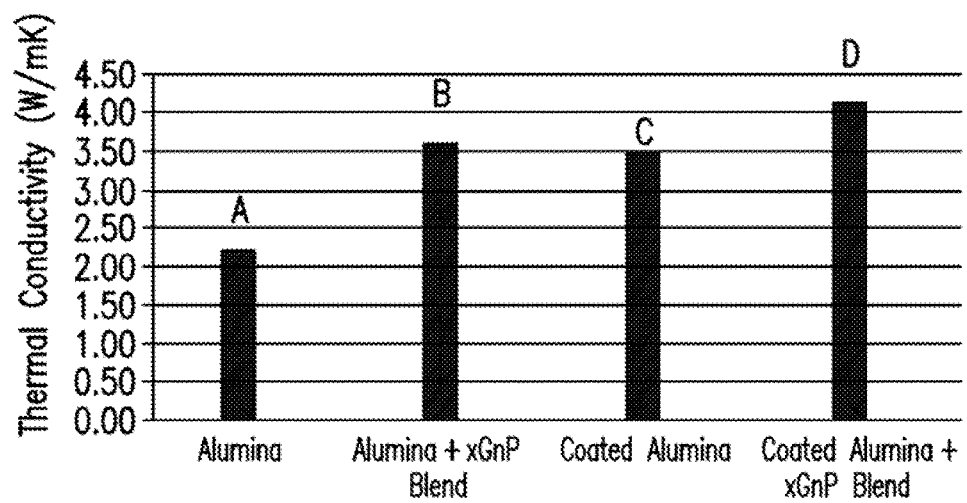
FIG. 8 is a graph showing thermal conductivity for alumina "A" versus alumina treated according to this invention "B" and coated alumina "C", and coated alumina and nanoplatelet blend "D".
Figure 9:
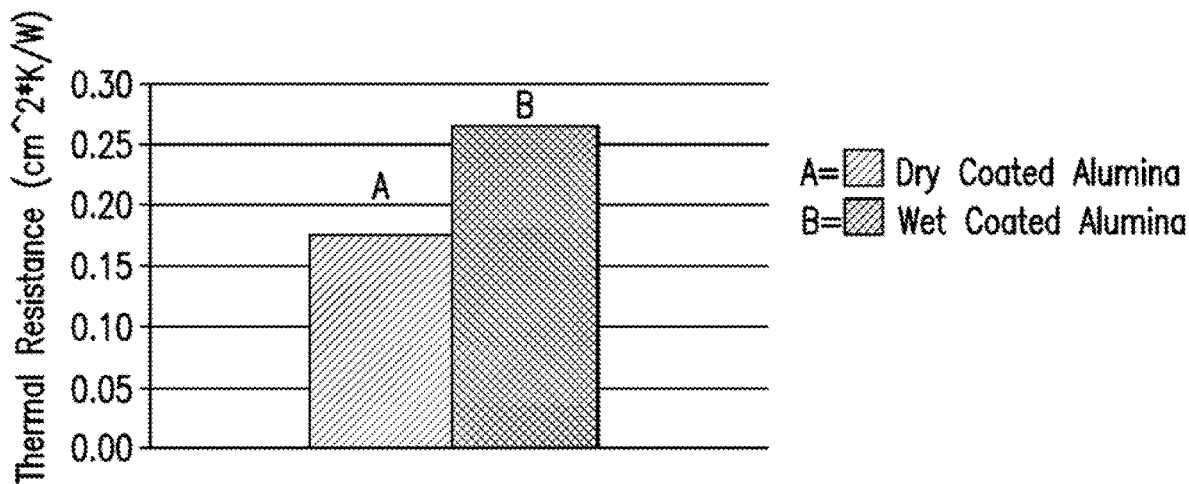
FIG. 9 is a graph showing thermal resistance of dry coated alumina versus wet coated alumina.
Figure 10:
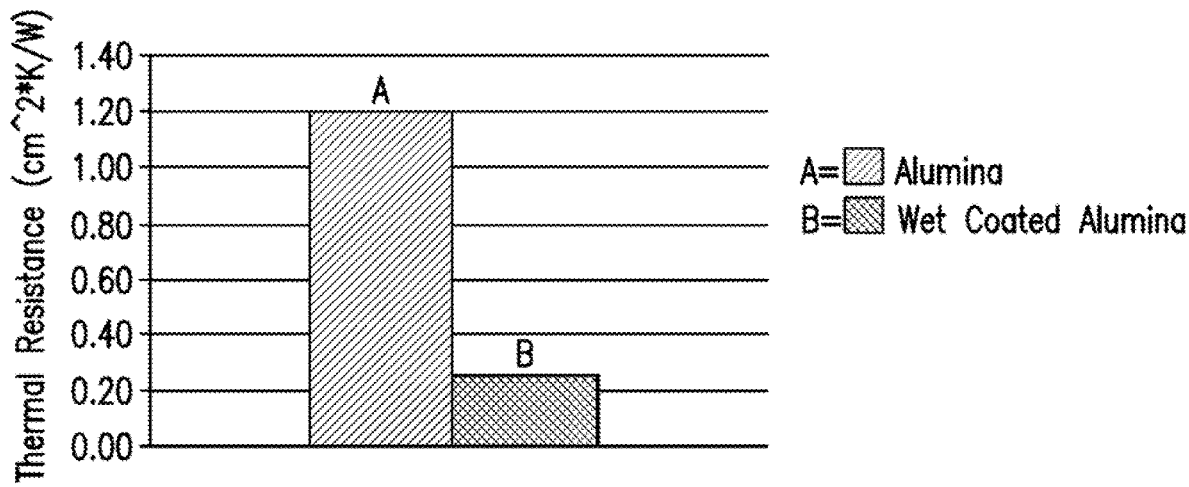
FIG. 10 is a graph showing thermal resistance of alumina and wet coated alumina.
Figure 11:
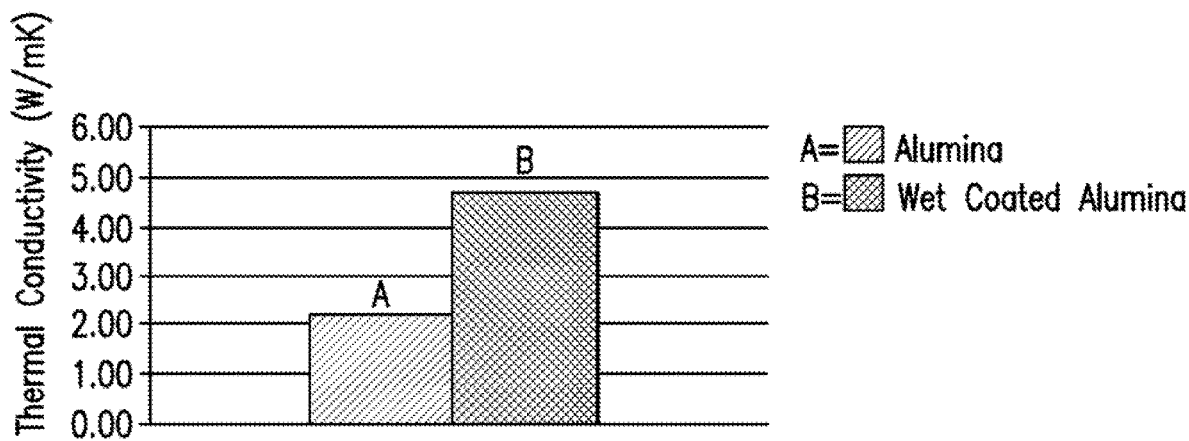
FIG. 11 is a graph showing thermal conductivity of alumina and wet coated alumina.

In one embodiment, this invention comprises a TIM grease made with graphene-nanoplatelet coated alumina fillers. Alumina fillers were coated with graphene-nanoplatelet by a process using a mechanical milling machine. The coating process was designed to effectively attach graphene nanoplatelets onto alumina filler without significantly pulverizing the graphene nanoplatelets or producing amorphous carbon coating. The coated alumina filler is shown in FIG. 4. The TIM made with graphene coated alumina filler showed significant increase in thermal conductivity (FIG. 5) and decrease in thermal resistivity (FIG. 6) as compared with bare alumina In another embodiment, graphene coating of fillers is achieved by a wet method. Graphene nanoplatelets and alumina are mixed together in a solution of appropriate organic solvent, where they are dispersed and agitated by ultrasonic mixing for 5 minutes. The solvent is then evaporated, leaving behind a homogeneous powder. The powder is dispersed into silicone oil in order to create a thermal grease. The resulting thermal grease shows enhanced thermal conductivity compared to a grease made with an equal loading of unmodified alumina, as shown in FIGS. 7 and 8.

In yet another embodiment, graphene nanoplatelets are added to a TIM grease together with graphene-coated alumina fillers. The additional graphene nanoplatelets serve to better bridge the fillers due to the 2-D and flexible features of graphene nanoplatelets. The flexible and flake-like graphene nanoplatelets can significantly increase the contact area of conductive fillers as illustrated in FIG. 3.

The term graphene as used in this invention shall include graphene nanoplatelets from fully exfoliated graphite to particles with thicknesses of less than 100 nm and/or number of layers less than 300, and preferably with thicknesses of less than 20 nm and/or number of layers less than 60.

EXAMPLES

Example 1

Milling

Graphene nanoplatelets and alumina were added together into a canister with nailing media, and ball milled for 20 minutes. The resulting homogeneous powder was dispersed into silicone oil in order to create thermal grease. The resulting thermal grease showed substantially increased thermal conductivity and lower thermal resistance compared to grease made with an equal loading of unmodified alumina. The grease also showed equal thermal conductivity and lower thermal resistance and viscosity compared to grease made by a simple mixture of the same graphene nanoplatelet and alumina mixture.

Example 2

Solution Processing

Graphene nanoplatelets and alumina were mixed together in a solution of appropriate organic solvent, where they were dispersed and agitated by ultrasonic mixing for 5 minutes.

The solvent was evaporated, leaving behind a homogeneous powder. The powder was dispersed into silicone oil in order to create a thermal grease. The resulting thermal grease showed enhanced thermal conductivity compared to a grease made with an equal loading of unmodified alumina.

Example 3

Graphene nanoplatelet coated alumina powder was prepared as described in example 1. This powder was dispersed into silicone oil together with unprocessed graphene nanoplatelet powder. The resulting thermal grease showed superior thermal conductivity compared to thermal greases prepared with an equal filler content of unmodified alumina, a mixture of unmodified alumina and unprocessed graphene nanoplatelet powder with the same graphene nanoplatelet to alumina ratio, or graphene nanoplatelet coated alumina with the same graphene nanoplatelet to alumina ratio. Shown in table I.

TABLE I

| Sample | Uncoated Alumina (g) | Unprocessed GnP (g) | Coated Alumina (g) | Coated GnP (g) | Silicone Oil (g) | Thermal Resistance (cm^2 * K/W) |
|---|---|---|---|---|---|---|
| Control 1 | 17 | 0 | 0 | 0 | 3 | 1.20 |
| Control 2 | 16.8 | 0.2 | 0 | 0 | 3 | 0.39 |
| Example 1 | 0 | 0 | 16.8 | 0.2 | 3 | 0.17 |
| Example 2 | 0 | 0 | 16.8 | 0.2 | 3 | 0.27 |
| Example 3 | 0 | 0.1 | 16.702 | 0.198 | 3 | 0.29 |

TABLE I-continued

| Total Sample Mass (g) | Thermal Conductivity (W/mK) |
|---|---|
| 20 | 2.22 |
| 20 | 3.65 |
| 20 | 3.61 |
| 20 | 4.76 |
| 20 | 4.27 |

What is claimed is:

1. A material comprising:
   ceramic filler particles;
   graphene, where the graphene is surrounding the ceramic filler particles and forming a coating thereon; and
   a resin matrix of at least one of silicone oil or hydrocarbon oil, said ceramic filler particles being dispersed in said resin matrix to form a grease without voids present between the coating on said particles and said resin matrix.

2. The material as claimed in claim 1 wherein the ceramic filler particles are selected from the group consisting of:
   a. an oxide,
   b. a carbide,
   c. a boride, and,
   d. nitride.

3. The material as claimed in claim 1 wherein the ceramic filler particles are selected from the group consisting of:
   a. alumina,
   b. zinc oxide,
   c. silica,
   d. boron nitride,
   e. silicon carbide,
   f. aluminum nitride,
   g. tin oxide,
   h. magnesium oxide,
   i. titanium oxide, and,
   j. beryllium oxide.

4. The material as claimed in claim 1 further comprising nanoplatelets, said nanoplatelets formed from at least one of graphene or boron nitride with the proviso that at least one of said graphene forming the coating on the ceramic filler particles or said graphene forming said nanoplatelets is prepared from the group consisting of:
   a. graphite,
   b. carbon black,
   c. activated carbon, and
   d. pitch.

5. The material as claimed in claim 4 wherein the nanoplatelets have a thickness below 100 nm.

6. The material as claimed in claim 4 wherein the nanoplatelets have a thickness below 50 nm.

7. The material as claimed in claim 4 wherein the nanoplatelets have a thickness below 25 nm.

8. The material as claimed in claim 4 wherein the nanoplatelets have a size below 500 nm.

9. The material as claimed in claim 4 wherein the nanoplatelets have a size below 10 nm.

10. A material comprising:
    spherical filler particles;
    graphene, where the graphene is surrounding the spherical filler particles and forming a coating thereon;
    a plurality of graphene nanoplatelets mixed with the spherical filler particles; and
    a resin matrix of at least of silicone oil or hydrocarbon oil, said spherical filler particles and said plurality of graphene nanoplatelets being dispersed in said resin matrix to form a grease without voids present between the coating on said particles and said resin matrix.

11. The thermal interface material as claimed in claim 10 wherein each of said plurality of graphene nanoplatelets have a thickness of below 100 nm.

12. The thermal interface material as claimed in claim 11 wherein each of said plurality of graphene nanoplatelets have a thickness of below 50 nm.

13. The material as claimed in claim 10 wherein each of said plurality of graphene nanoplatelets have a thickness of one carbon atom.

14. The thermal interface material as claimed in claim 11 wherein each of said plurality of graphene nanoplatelets have a thickness of below 10 nm.

15. A method of providing a thermal interface composite, said method comprising:
    A. providing a first substrate that is a heat sink;
    B. providing a second substrate that is a heat source;
    C. placing a thermal interface material as claimed in claim 1 between said first substrate and said second substrate.

16. A method of providing a thermal interface composite, said method comprising:
    A. providing a first substrate that is a heat sink;
    B. providing a second substrate that is a heat source;
    C. placing a thermal interface material as claimed in claim 10 between said first substrate and said second substrate.

17. A composite structure comprising:
    a solid heat source;
    a solid heat sink;
    a thermal interface material as claimed in claim 1 contained between said solid heat source and said solid heat sink.

18. A composite structure comprising:
    a solid heat source;
    a solid heat sink;
    a thermal interface material as claimed in claim 10 contained between said solid heat source and said solid heat sink.

* * * * *